(12) United States Patent
Yan et al.

(10) Patent No.: US 7,625,945 B2
(45) Date of Patent: *Dec. 1, 2009

(54) ANDROGRAPHOLIDE AND ANALOGUES AS INHIBITORS OF TNFα AND IL-1β EXPRESSION

(75) Inventors: Xiaoqiang Yan, Shanghai (CN); Tao Wang, Shanghai (CN); Zhiming Ma, Suzhou (CN); Ke Pan, Shanghai (CN); Weihan Zhang, Shanghai (CN); Jianrong Hong, Shanghai (CN); Jeff Duan, Shanghai (CN); Yu Cai, Shanghai (CN)

(73) Assignee: Hutchison MediPharma Enterprises Ltd., Nassau (BS)

( * ) Notice: Subject to any disclaimer, the term of this patent is extended or adjusted under 35 U.S.C. 154(b) by 441 days.

This patent is subject to a terminal disclaimer.

(21) Appl. No.: 11/078,198

(22) Filed: Mar. 11, 2005

(65) Prior Publication Data

US 2005/0215628 A1    Sep. 29, 2005

Related U.S. Application Data

(60) Provisional application No. 60/552,329, filed on Mar. 11, 2004.

(51) Int. Cl.
*A61K 31/341* (2006.01)
(52) U.S. Cl. .................................................. 514/473
(58) Field of Classification Search ........................ None
See application file for complete search history.

(56) References Cited

U.S. PATENT DOCUMENTS

2002/0068098 A1* 6/2002 Babish et al. ............... 424/725
2004/0151792 A1* 8/2004 Tripp et al. ................. 424/745

OTHER PUBLICATIONS

Zhang et al., Phytother. Research, 13(2) (1999) pp. 157-159.*
Achike et al., Clinical & Experimental Pharmacology & Physiology, 30 (2003), 605-615.*
Mahadevan et al., Am. J. Gastroenterology, (Apr. 2002), 97(4): 910-4 (Abstract).*
Mishra et al., Pharmacognosy Reviews, 1(2), (Jul.-Dec. 2007) 283-298.*
Deng W.L. et al., Chinese Pharm. Bull. 17:195-198, 1982.
Habtemarian S., Andrographolide Inhibits the Tumor Necrosis factor-α-induced Upregulation of ICAM-1 Expression and Endothelial-monocyte Adhesion, Phytotherapy Research, 12:37-40, 1998.
Madav S. et al., Anti-inflammatory activity of andrographolide, Fitoterapia, 67:452-458, 1996.
Matsuda et al., Studies on the cell differentiation induces of *Andrographis paniculata*, Tennen Yuki Kagobutsu Toronkai Koen Yoshishu, 33:433-440, 1991.
Rajagopal S. et al., Andrographolide, a potential cancer therapeutic agent isolated from *Andrographis paniculata*, Journal of Experimental Therapeutics and Oncology 3:147-158, 2003.
Zhang C.Y. et al., Effects of 14-Deoxyandrographolide and 14-Deoxy-11, 12-Didehydroandrographolide on Nitric Oxide Production in Cultured Human Endothelial Cells, Phytotherapy Research, 13:157-159, 1999.
Wang, et al., "Andrographolide reduces inflammation-mediated dopaminergic neurodegeneration in mesencephalic neuron-glia cultures by inhibiting microglial activation", Journal of Pharmacology and Experimental Therapeutics, 308(3):915-983, 2004, abstract.
Panossian, et al., "Effect of andrographolide and Kan Jang-fixed combination of extract SHA-10 and extract SHE-3-on proliferation of human lymphocytes, production of cytokines and immune activation markers in the whole blood cells culture", Phytomedicine, 9(7):598-605, 2002, abstract.
Peng, et al., "Modulation of Lianbizi injection (andrographolide) on some immune functions", Zhongguo Zhongyao Zazhi, 27(2):147-150, 2002, abstract.
See, et al., "Increased tumor necrosis factor alpha (TNF-alpha) and natural killer cell (NK) function using an integrative approach in late stage cancers", Immunological Investigations, 31(2):137-153, 2002, abstract.
Kumar, et al., "Anticancer and immunomodulatory potential of DRF-3188, an analogue of andrographolide", Novel Compounds from Natural Products in the New Millennium, 205-216, 2004, abstract.
Habtemariam, S., "Natural Inhibitors of Tumor Necrosis Factor-α Production, Secretion and Function"Planta Med 66:303-313, 2000.
Xia, "Andrographolide Attenuates Inflammation by Inhibition of NF-kB Activation Through Covalent Modification of Reduced Cysteine 62 of p50¹" The Journal of Immunology, 4207-4217, 2004.

* cited by examiner

*Primary Examiner*—Phyllis G. Spivack
(74) *Attorney, Agent, or Firm*—Occhiuti Rohlicek & Tsao LLP

(57) ABSTRACT

This invention relates to a method of inhibiting the expression of TNFα or IL-1β with a compound of the following formula:

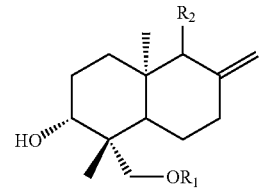

wherein $R_1$ and $R_2$ are defined herein. It also relates to is a method of treating inflammatory bowel disease with such a compound.

9 Claims, No Drawings

ANDROGRAPHOLIDE AND ANALOGUES AS INHIBITORS OF TNFα AND IL-1β EXPRESSION

CROSS REFERENCE TO RELATED APPLICATIONS

Pursuant to 35 USC § 119(e), this application claims priority to U.S. Provisional Application Ser. No. 60/552,329, filed Mar. 11, 2004, the contents of which are incorporated herein by reference.

BACKGROUND

Tumor necrosis factor alpha (TNFα), a mononuclear cytokine, is predominately produced by monocytes and macrophages. It possesses various biological activities: (1) killing cancer cells or inhibiting growth of cancer cells, (2) enhancing the phagocytosis of neutrophilic granulocytes, (3) up-regulating the production of peroxide, and (4) killing infection pathogens.

TNFα is a potential target for treating disorders related to the expression of TNFα. These disorders include, but are not limited to, rheumatoid arthritis, juvenile rheumatoid arthritis, osteoarthritis, spondyloarthropathies, inflammatory bowel disease (including Crohn's disease and ulcerative colitis), chronic heart failure, diabetes mellitus, systemic lupus erythematosus, scleroderma, sarcoidosis, polymyositis/dermatomyositis, psoriasis, multiple myeloma, myelodysplastic syndrome, acute myelogenous leukemia, Parkinson's disease, AIDS dementia complex, Alzheimer's disease, depression, sepsis, pyoderma gangrenosum, hematosepsis, septic shock, Behcet's syndrome, graft-versus-host disease, uveitis, Wegener's granulomatosis, Sjogren's syndrome, chronic obstructive pulmonary disease, asthma, acute pancreatitis, periodontal disease, cachexia, cancer, central nervous system injury, viral respiratory disease, and obesity (Ogata H, Hibi T. et al *Curr Pharm Des.* 2003; 9(14): 1107-13; Moller D R. et al *J Intern Med.* 2003 January; 253(1): 31-40; Taylor P C. Et al *Curr Pharm Des.* 2003; 9(14): 1095-106; Wilkinson N et al *Arch Dis Child.* 2003 March; 88(3): 186-91; Nishimura F et al *J Periodontol.* 2003 January; 74(1): 97-102; Weinberg J M et al *Cutis.* 2003 January; 71(1): 41-5; Burnham E et al *Crit Care Med.* 2001 March; 29(3): 690-1; Sack M. et al *Pharmacol Ther.* 2002 April-May; 94(1-2): 123-35; Barnes P J. Et al *Annu Rev Pharmacol Toxicol.* 2002; 42:81-98; Mageed R A et al *Lupus.* 2002; 11(12): 850-5; Tsimberidou A M et al *Expert Rev Anticancer Ther.* 2002 June; 2(3): 277-86; Muller T. et al *Curr Opin Investig Drugs.* 2002 December; 3(12): 1763-7; Calandra T et al *Curr Clin Top Infect Dis.* 2002; 22:1-23; Girolomoni G et al *Curr Opin Investig Drugs.* 2002 November; 3(11): 1590-5; Tutuncu Z et al *Clin Exp Rheumatol.* 2002 November-December; 20(6 Suppl 28): S146-51; Braun J et al *Best Pract Res Clin Rheumatol.* 2002 September; 16(4): 631-51; Barnes P J. Et al *Novartis Found Symp.* 2001; 234:255-67; discussion 267-72; Brady M, et al *Baillieres Best Pract Res Clin Gastroenterol.* 1999 July; 13(2): 265-89; Goldring M B. et al *Expert Opin Biol Ther.* 2001 September; 1(5): 817-29; Mariette X. *Rev Prat.* 2003 Mar. 1; 53(5): 507-11; Sharma R et al *Int J Cardiol.* 2002 September; 85(1): 161-71; Wang C X et al *Prog Neurobiol.* 2002 June; 67(2): 161-72; Van Reeth K et al *Vet Immunol Immunopathol.* 2002 Sep. 10; 87(3-4): 161-8; Leonard B E et al *Int J Dev Neurosci.* 2001 June; 19(3): 305-12; Hays S J et al *Curr Pharm Des.* 1998 August; 4(4): 335-48.).

Interleukin-1 beta (IL-1β), a cytokine secreted by cells such as monocyte macrophages and dendritic cells, mediates a wide range of immune and inflammatory responses. Modulating the expression of IL-1β leads to treatment of a variety of disorders, such as rheumatoid arthritis, hematosepsis, periodontal disease, chronic heart failure, polymyositis/dermatomyositis, acute pancreatitis, chronic obstructive pulmonary disease, Alzheimer's disease, osteoarthritis, bacterial infections, multiple myeloma, myelodysplastic syndrome, uveitis, central nervous system injury, viral respiratory disease, asthma, depression, and scleroderma (Taylor P C. et al *Curr Pharm Des.* 2003; 9(14): 1095-106; Dellinger R P et al *Clin Infect Dis.* 2003 May 15; 36(10): 1259-65; Takashiba S et al *J Periodontol.* 2003 January; 74(1): 103-10; Diwan A, et al *Curr Mol Med.* 2003 March; 3(2): 161-82; Lundberg I E, et al *Rheum Dis Clin North Am.* 2002 November; 28(4): 799-822; Makhija R, et al *J Hepatobiliary Pancreat Surg.* 2002; 9(4): 401-10; Chung K F. Et al *Eur Respir J Suppl.* 2001 December; 34:50s-59s; Hallegua D S, et al *Ann Rheum Dis.* 2002 November; 61(11): 960-7; Goldring M B. Et al *Expert Opin Biol Ther.* 2001 September; 1(5): 817-29; Mrak R E, Griffin W S. Et al *Neurobiol Aging.* 2001 November-December; 22(6): 903-8; Brady M, et al *Baillieres Best Pract Res Clin Gastroenterol.* 1999 July; 13(2): 265-89; Van der Meer J W, et al *Ann N Y Acad Sci.* 1998 Sep. 29; 856:243-51; Rameshwar P et al *Acta Haematol.* 2003; 109(1): 1-10; de Kozak Y et al *Int Rev Immunol.* 2002 March-June; 21(2-3): 231-53; Wang C X et al *Prog Neurobiol.* 2002 June; 67(2): 161-72; Van Reeth K et al *Vet Immunol Immunopathol.* 2002 Sep. 10; 87(3-4): 161-8; Stirling R G et al *Br Med Bull.* 2000; 56(4): 1037-53; Leonard B E et al *Int J Dev Neurosci.* 2001 June; 19(3): 305-12; Allan S M et al *Ann N Y Acad Sci.* 2000; 917:84-93; and Cafagna D et al *Minerva Med.* 1998 May; 89(5): 153-61).

SUMMARY

This invention is based on surprising discoveries that andrographilide and its analogues inhibit the expression of both TNFα and IL-1β and that andrographilide alleviates DNBS-induced colitis in rats.

One aspect of this invention relates to a method of inhibiting the expression of TNFα or IL-1β by contacting TNFα or IL-1β with an effective amount of one or more of the compounds of Formula I:

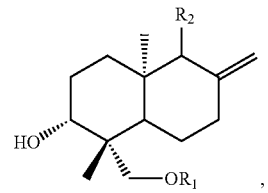

Formula I wherein $R_1$ is hydrogen, alkyl, aryl, cyclyl, or heterocyclyl; and $R_2$ is

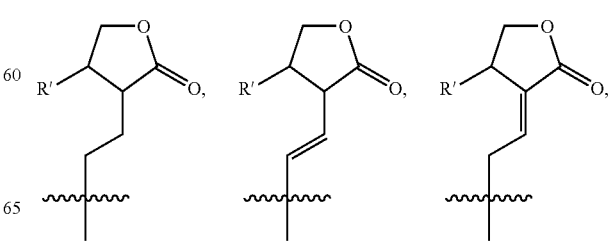

-continued

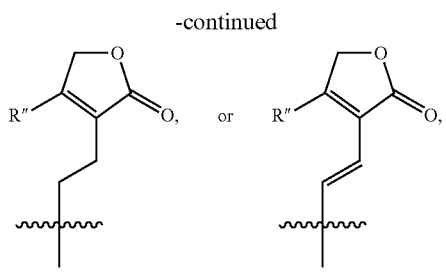

in which R' is H, alkyl, cyclyl, aryl, heteroaryl, alkoxy, halo, amino, or hydroxy; and R" is H, alkyl, cyclyl, aryl, heteroaryl, alkoxy, amino, or halo.

Referring to Formula I, one subset of the compounds are featured by that $R_1$ is H and $R_2$ is

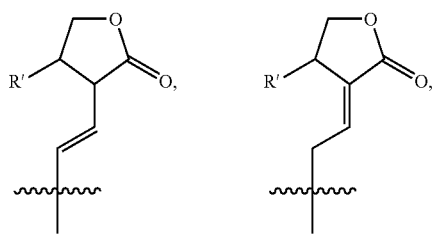

or

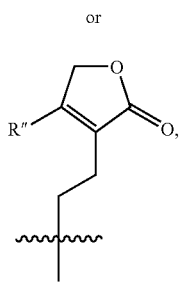

in which R' is H or hydroxy and R" is H.

Set forth below are four exemplary compounds that can be used to practice the above methods:

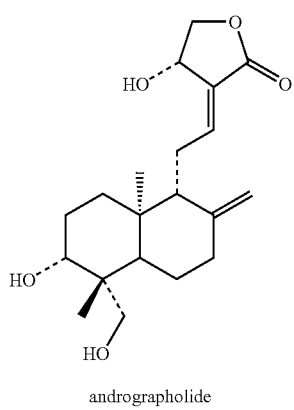

andrographolide

-continued

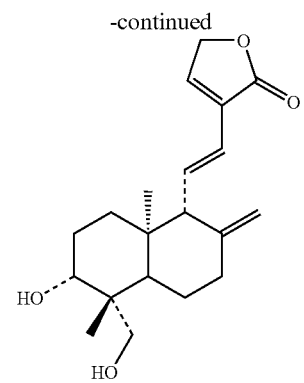

14-deoxy-11,12-dehydrogen-andrographolide

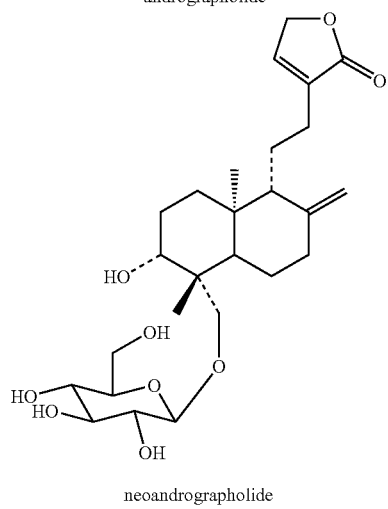

neoandrographolide

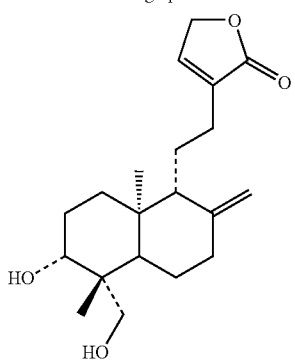

14-deoxy-andrographolide

Another aspect of this invention relates to a method of treating a disorder related to TNFα or IL-1β, i.e., inflammatory bowel disease (including Crohn's disease and ulcerative colitis), chronic heart failure, diabetes mellitus, systemic lupus erythematosus, polymyositis/dermatomyositis, psoriasis, acute myelogenous leukemia, AIDS dementia complex, hematosepsis, septic shock, graft-versus-host disease, uveitis, asthma, acute pancreatitis, or periodontal disease. The method includes administering to a subject in need of the treatment an effective amount of one or more of the compounds of Formula I, e.g., any of the four exemplary compounds shown above.

Also within the scope of this invention is a pharmaceutical composition containing a compound of Formula I and a pharmaceutically acceptable carrier, as well as use of the composition for the manufacture of a medicament for treating any above-described disorder.

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cyclyl" refers to a saturated and partially unsaturated cyclic hydrocarbon group having 3 to 12 carbons. Examples of cyclyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocyclyl" refers to a nonaromatic 5-8 membered monocyclic, 8-12 membered bicyclic, or 11-14 membered tricyclic ring system having one or more heteroatoms (such as O, N, or S). Examples of heterocyclyl groups include, but are not limited to, piperazinyl, pyrrolidinyl, dioxanyl, morpholinyl, tetrahydrofuranyl, glucosyl, mannosyl, galactosyl, fructosyl, inositolyl, sorbosyl, talosyl, altrosyl, allosyl, idosyl, rhamnosyl, arabinosyl, xylosyl, ribosyl, and xylulosyl.

Alkyl, cyclyl, heterocyclyl, aryl, heteroaryl, and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl may be further substituted.

The details of one or more embodiments of the invention are set forth in the accompanying description below. Other features, objects, and advantages of the invention will be apparent from the description and the claims.

DETAILED DESCRIPTION

Among the compounds described above, andrographolide and several of its analogues can be isolated from *Andrographis paniculata* (see, e.g., Balmain A et al *J. Chem. Soc. Perkin. Trans. I* 1973: 1247-1251). Andorgrapholide is also commercially available. Other compounds can be synthesized from andrographolide and its naturally occurring analogues by simple chemical transformations. In the synthetic process, protecting group methodologies may be adopted. The chemical transformations and protecting group methodologies (protection and deprotection) useful in synthesizing applicable compounds are well known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, Fieser and *Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds described above include their pharmaceutically acceptable salts and prodrugs, if applicable. Such a salt can be formed between and a positively charged ionic group in an above-described compound (e.g., ammonium) and a negatively charged counterion (e.g., chloride, bromide, or iodide). Likewise, a negatively charged ionic group in an above-described compound can also form a salt with a positively charged counterion. Examples of prodrugs include esters and other pharmaceutically acceptable compounds, which, upon administration to a subject, are capable of providing the compounds described above.

In addition, the compounds described above have one or more double bonds, and one or more asymmetric centers. They can occur as racemates, racemic mixtures, single enantiomers, individual diastereomers, diastereomeric mixtures, and cis- or trans- or E- or Z-double isomeric forms.

One aspect of this invention is a method for inhibiting the expression of TNFα or IL-1β. The method includes contacting TNFα or IL-1β with an effective amount of one or more of the compounds described above. The term "an effective amount" is the amount of the compound which is required to confer the desired effect. Effective amounts may vary, as recognized by those skilled in the art, depending on route of administration, excipient usage, and the possibility of co-usage with other agents.

As the compounds described above inhibit the expression of TNFα or IL-1β, they can be used to treat a disorder caused by over-expression of TNFα or IL-1β. Thus, also within the scope of this invention is a method of treating a disorder related to TNFα or IL-1β over-expression, i.e., inflammatory bowel disease (including Crohn's disease and ulcerative colitis), chronic heart failure, diabetes mellitus, systemic lupus erythematosus, polymyositis/dermatomyositis, psoriasis, acute myelogenous leukemia, AIDS dementia complex, hematosepsis, septic shock, graft-versus-host disease, uveitis, asthma, acute pancreatitis, or periodontal disease. The method includes administering to a subject in need of the treatment an effective amount of one of the compounds described above. The term "treating" refers to the application or administration of a composition including the compound to a subject, who has one of the above-mentioned disorders, a symptom of the disorder, or a predisposition toward the disorder, with the purpose to cure, heal, alleviate, relieve, alter, remedy, ameliorate, improve, or affect the disorder, the symptoms of the disorder, or the predisposition toward the disorder.

To practice the treatment method of this invention, one or more of the compounds described above are mixed with a pharmaceutically acceptable carrier and then administered orally, rectally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A composition for oral administration can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

One or more active compounds can be administered rectally. One example is a suppository, which comprises the active compounds with a suppository base. Suitable suppository bases are, for example, natural or synthetic triglycerides, or paraffin hydrocarbons. Another example is a gelatin rectal capsule which comprise the active compounds and a base. Possible base materials include, for example, liquid triglycerides, polyethylene glycols, or paraffin hydrocarbons.

A composition that are applied to the skin can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil.

Ointments may be formulated by mixing a solution of the active ingredient in a vegetable oil, such as almond oil, with warm soft paraffin and allowing the mixture to cool. An example of such an ointment is one which includes about 30% almond and about 70% white soft paraffin by weight.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with the active compounds), can be utilized as pharmaceutical excipients for delivery of the active compounds. Examples of other carriers include colloidal silicon dioxide, magnesium stearate, cellulose, sodium lauryl sulfate, and D&C Yellow # 10.

A suitable in vitro assay can be used to preliminarily evaluate the efficacy of any of the above-described compounds in inhibiting the expression of TNFα or IL-1β expression. Compounds that demonstrate high activity in the preliminary screening can further be screened by in vivo assays. For example, a test compound can administered to an animal (e.g., a mouse model) having inflammatory bowel disease and its therapeutic effects are then accessed. Based on the results, appropriate dosage ranges and administration routes can also be determined.

Without further elaboration, it is believed that the above description has adequately enabled the present invention. The following specific examples are, therefore, to be construed as merely illustrative, and not limitative of the remainder of the disclosure in any way whatsoever. All of the publications, including patents, cited herein are hereby incorporated by reference in their entirety.

In Vitro Assay

Four test compounds, andrographolide (National Institute for the Control of Pharmaceutical And Biological Products), neoandrographolide (China Pharmaceutical University), 14-deoxy-11,12-dehydrogen-andrographolide (China Pharmaceutical University), and 14-deoxy-andrographolide (China Pharmaceutical University) were dissolved in dimethylsulfoxide, respectively, to provide various test solutions.

Peripheral blood monocytes (PBMC) were isolated from fresh blood using a Ficoll-Paque Plus reagent (Amersham Bioscience) according to the protocol recommended by the manufacturer. The cells were suspended in RPMI 1640 media containing 10% fetal bovine serum at a concentration of $1\times10^5$ cells/ml and seeded in 96-well plate ($1\times10^4$ cells total in each well). Each reaction was carried out in three wells.

10 µl of test solutions in was added into wells (final concentrations of the test compound: 0.1, 0.3, 1, 3, 10, and 30 µg/ml). Dexamethason (CalBiochem, final concentration: 10 µM) was used as positive control. 10 µl of media was used as a negative control. The plate was incubated at 37° C. under 5% $CO_2$ for 15 minutes. After 10 µl aliquots of 100 µg/ml lipopolysaccharide (LPS) were added to all wells except for the negative controls, the plate was incubated at 37° C. under 5% $CO_2$ overnight.

The plate was spun at 1000 rpm for 15 minutes and the supernatants were collected. Concentrations of TNFα and IL-1β were measured using the TNFα ELISA (Enzyme Linked Immunosorbent Assay) Kit and IL1-β ELISA Kit (Jingmei Bioengineer Technology).

The inhibition ratio was calculated as follows:

$$\text{Inhibition Ratio } (\%) = \left(1 - \frac{C_{test\ compound} - C_{Control}}{C_{LPS} - C_{Control}}\right) \times 100\%$$

where $C_{test\ compound}$ is the concentration of TNFα or IL-1β in PBMC cells treated with a test compound and LPS, $C_{LPS}$ is the concentration of TNFα or IL-1β in PBMC cells treated with LPS and dexamethason, and $C_{Control}$ is the concentration of TNFα or IL-1β in PBMC cells without being treated with LPS or a test compound.

The results showed that all four compounds significantly inhibited the expression of both TNFα and IL-1β.

In Vivo Assay

Male Wistar rats (170-190 g, provided by Chinese academy of science animal center, Shanghai) were housed (7~8 rats per cage) in a controlled environment and fed with standard rodent chow and water. Distal colitis was induced to the rats according to the procedure described in Hogaboam C. M., *European Journal of Pharmacology*, 1996, 309: 261-269. Briefly, the rats were anaesthetized with 1% pentobarbital sodium. 2,4-Dinitrobenzene sulfonic acid (DNBS) in 0.25 ml of 30% ethanol (v/v) was introduced into the colon (8 cm proximal to the anus) via a PE 50 cannula. In the control group (blank-control), 30% ethanol (v/v), in stead of DNBS in ethanol, was introduced.

Andrographolide (10 mg/kg, i.p.) was administered to a group of DNBS-treated rats 24 hours and 2 hours prior to the colitis induction and once daily thereafter for 5 days.

The rats were weighed daily. All rats were sacrificed 6 days after the colitis induction, and colon, spleen, and thymus were removed and weighed. The colon weight/body weight ratio, spleen weight/body weight ratio, and thymus weight/body weight ratio were calculated.

Samples of colon tissues located precisely 2 cm above the anal canal were obtained, fixed in 10% neutral-buffered formalin, embedded in paraffin, sectioned, and stained with hematoxylin/eosin. The samples were examined under microscope to determine severity of the lesions.

The rats given only DNBS manifested severe diarrhea, a sustained weight loss, and a marked increase of colon weight/body weight ratio. Treatment with andrographolide (10 mg/kg) for 6 days alleviated wasting syndrome and decreased colon weight/body weight ratio.

The microscopic examination showed that the colons of the rats given DNBS and not andrographolide had transmural inflammation in all layers of their bowel wall. It also showed marked infiltration of inflammation cells, epithelial cell loss, patchy ulceration, and pronounced depletion of mucin-producing goblet cells in the examined colon tissues. The colons of the rats given DNBS and treated with andragrapholide showed much less severe inflammation. In these colons, the bowel wall was sleek and did not adhere to surrounding tissues. Andragrapholide effectively alleviated or even cured DNBS-induced colitis.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to andrographolide can be made, screened for their inhibitory activities against the expression TNFα or IL-1β and treating TNFα or IL-1β related disorders and used to practice this invention. Thus, other embodiments are also within the claims.

What is claimed is:

1. A method of treating inflammatory bowel disease, comprising administering to a subject in need thereof an effective amount of a pharmaceutical composition containing a compound of the following formula:

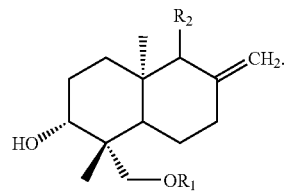

in which
  $R_1$ is hydrogen, alkyl, aryl, or cyclyl; and
  $R_2$ is

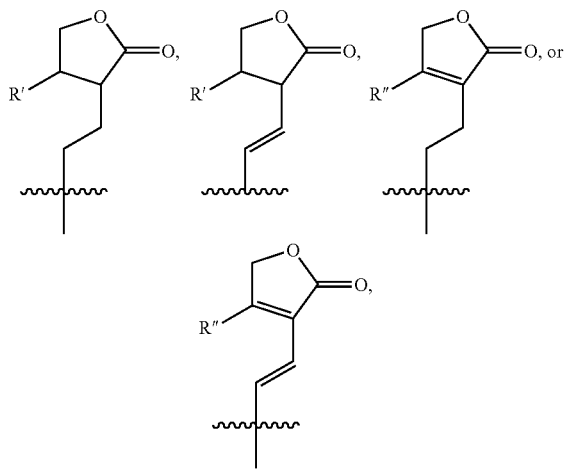

in which R' is H, alkyl, cyclyl, aryl, alkoxy, halo, amino, or hydroxy; and R" is H, alkyl, cyclyl, aryl, alkoxy, amino, or halo;
wherein said compound is the only effective agent in the composition for treating the inflammatory bowel disease.

2. The method of claim 1, wherein $R_1$ is H.

3. The method of claim 2, wherein $R_2$ is

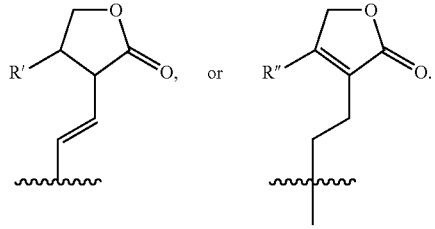

4. The method of claim 3, wherein R' is H or hydroxy and R" is H.

5. The method of claim 1, wherein the compound is 14-deoxyandrographolide.

6. The method of claim 1, wherein the compound is 14-deoxy-11,12-didehydrogen-andrographolide.

7. The method of claim 1, wherein the compound is neoandrographolide.

8. The method of claim 1, wherein the inflammatory bowel disease is Crohn's disease.

9. The method of claim 1, wherein the inflammatory bow disease is ulcerative colitis.

* * * * *